United States Patent
Golborn et al.

[11] 3,935,162
[45] Jan. 27, 1976

[54] DIALKYL AROMATIC AMIDOMETHYL PHOSPHONATE FLAME RETARDANTS

[75] Inventors: Peter Golborn, Lewiston; James J. Duffy, Buffalo, both of N.Y.

[73] Assignee: Hooker Chemicals & Plastics Corporation, Niagara Falls, N.Y.

[22] Filed: Dec. 11, 1974

[21] Appl. No.: 531,646

Related U.S. Application Data

[62] Division of Ser. No. 393,868, Sept. 4, 1973, Pat. No. 3,895,161, which is a division of Ser. No. 239,784, March 30, 1972, Pat. No. 3,803,269.

[52] U.S. Cl. 260/45.9 NC; 106/15 FP; 260/2.5 AJ; 260/45.75 B
[51] Int. Cl.² .......................................... C08G 6/00
[58] Field of Search ............ 260/45.9 NP, 45.9 NC, 2.5 AJ; 106/15 FP

[56] References Cited
UNITED STATES PATENTS 3,803,269   4/1974   Golborn et al. ............. 260/45.9 NC

*Primary Examiner*—V. P. Hoke
*Attorney, Agent, or Firm*—Peter F. Casella; William J. Crossetta, Jr.

[57] ABSTRACT

New flame retardant materials are disclosed having applied thereto compounds of the formula:

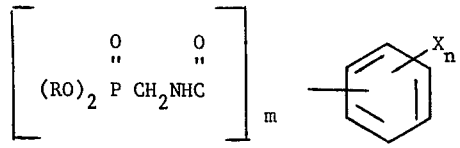

wherein R is selected from the group consisting of phenyl, lower alkenyl and halogen substituted and unsubstituted lower alkyl of 1–6 carbon atoms, X is selected from the group consisting of chlorine, bromine and lower alkyl of 1–6 carbon atoms, $m$ is an integer from 1–4 and $n$ is an integer from 0–5, provided that the sum of $m$ and $n$ is not greater than 6 and when $m$ is 1, $n$ is greater than 0.

15 Claims, No Drawings

DIALKYL AROMATIC AMIDOMETHYL PHOSPHONATE FLAME RETARDANTS

This is a division of application Ser. No. 393,868, filed Sept. 4, 1973 now U.S. Pat. No. 3,895,161, issued July 15, 1975 which in turn is a division of Ser. No. 239,784 filed Mar. 30, 1972, now U.S. Pat. No. 3,803,269 issued Apr. 9, 1974.

FIELD OF THE INVENTION

This invention relates to novel compounds of the formula

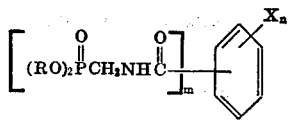

wherein R is selected from the group consisting of phenyl, lower alkenyl, and halogen substituted and unsubstituted lower alkyl of 1–6 carbon atoms, X is selected from the group consisting of chlorine, bromine and lower alkyl of 1–6 carbon atoms, $m$ is an integer from 1–4 and $n$ is an integer from 0–5, provided that the sum of $m$ and $n$ is not greater than 6 and when $m$ is 1, X is greater than 0. The invention includes methods of applying the above novel compounds to normally flammable textiles, thermoplastic, thermosetting, and elastomeric resin compositions so as to render them flame retardant.

BACKGROUND OF THE INVENTION

Many flame retarding agents and methods of application have been developed in attempts to obtain flame resistant textile materials and thermoplastic, thermosetting, and elastomeric resin compositions.

Flame retardant textiles have been produced by depositing metal oxides, within or on the textile fibers, by the successive precipitation of ferric oxides and a mixture of tungstic acid and stannic oxide or by successive deposition of antimony trioxide and titanium dioxide. Such posprocesses require plural treatment baths in which strongly acidic solutions are employed thus posing the problem of possible textile degradation. Furthermore, metal oxide coatings on textile materials create difficulties in subsequent dyeing processes which deleteriously affect the hand of the finished product. Another process involves the use of a single processing bath wherein a dispersion of a chlorinated hydrocarbon and finely divided antimony oxide is padded on the textile material. Near the textile combustion temperature antimony oxide will react with hydrogen chloride, generated by degradation of the chlorinated hydrocarbon, to form antimony oxychloride which acts to suppress flame. This combination of a chlorinated hydrocarbon and finely divided antimony oxide are not acceptable finishes for closely woven textiles as they deleteriously affect the hand of the finished product. A further process for imparting flame resistance to cellulosic materials is by the esterification of the cellulose with diammonium hydrogen orthophosphate. Textile products so treated however are subjected to metathesis reaction with cations during washing, and must be regenerated by reacting the wash product with an ammonium chloride solution.

The production of thermoplastic, thermosetting, and elastomeric resin compositions which are flame retardant is of considerable commercial importance. For example, such articles as castings, moldings, foamed or laminated structures and the like are required, or are at least desired, to be resistant to fire and flame and to possess the ability to endure heat without deterioration. The use of various materials incorporated into thermoplastic, thermosetting and elastomeric resins so as to improve the flame retardancy thereof has been known. Many compounds have been commercially available for such use, among them being chlorostyrene copolymers, chlorinated paraffin wax in admixture with triphenyl styrene, chlorinated paraffins and aliphatic antimonical compounds, as well as antimony oxide-chlorinated hydrocarbon mixtures. A problem associated with these compounds has been however, the fact that generally a large amount, i.e., upwards of 35% of additive, must be incorporated into the resin in order to make it sufficiently flame retardant. Such large amounts of additive may deleteriously affect the physical characteristics of the thermoplastic resin, as well as substantially complicating and increasing the cost of preparation thereof. A further problem is that these prior art additives tend to crystallize or oil out of the resin after a relatively short time of incorporation. The present invention relates to a group of compounds which may be added to thermoplastic resins in relatively small amounts and still produce satisfactory flame retardant compositions which will not crystallize nor oil out of the resin after incorporation therein.

OBJECTS OF THE INVENTION

It is, therefore, a principal object of this invention to provide novel compounds of the formula:

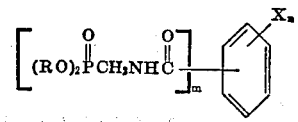

wherein R is selected from the group consisting of phenyl, lower alkenyl and halogen substituted and unsubstituted lower alkyl of 1–6 carbon atoms. X is selected from the group consisting of chlorine, bromine and lower alkyl of 1–6 carbon atoms, $m$ is an integer from 1–4 and $n$ is an integer from 0–5, provided that the sum of $m$ and $n$ is not greater than 6 and when $m$ is 1, $n$ is greater than 0.

It is also an object of this invention to provide flame retarding textile materials comprising normally flammable cellulosic, proteinaceous or analogous man-made materials. Another object is to provide a method for treating normally flammable cellulosic, proteinaceous or analogous man-made materials to render them flame retardant. Another object is to provide flame retarding thermoplastic, thermosetting or elastomeric resin compositions comprising normally flammable resin materials. A further object is to provide process for heating normally flammable thermoplastic, thermosetting or elastomeric resin compositions to render them flame retardant. A particular object is to devise a composition comprising normally flammable cellulosic, proteinaceous or analogous man-made materials and an effective flame retardant amount of the compound represent by the formula

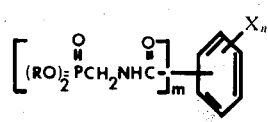

wherein R, X, m and n are as above described.

A further particular object is to devise a composition comprising normally flammable thermoplastic, thermosetting or elastomeric polymers and an effective flame retarding amount of the before described novel compound.

These and other objects of the present invention will be obvious from the following description.

DESCRIPTION OF THE INVENTION

In accordance with this invention there are provided novel compounds, for imparting flame retardancy to textiles and resin materials, of the formula

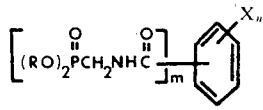

wherein R is selected from the group consisting of phenyl, lower alkenyl and halogen substituted and unsubstituted lower alkyl of 1–6 carbon atoms. X is selected from the group consisting of chlorine, bromine and lower alkyl of 1–6 carbon atoms, m is an integer from 1–4 and n is an integer from 0–5, provided that the sum of m and n is not greater than 6 and when m is 1, n is greater than 0.

More specifically, the preferred compounds of the present invention include these compounds wherein R is lower alkyl, allyl, chlorinated alkyl or phenyl, and X is chlorine, bromine or methyl.

Illustrative examples of compounds of the present invention include, for instance, compounds of the general formula such as

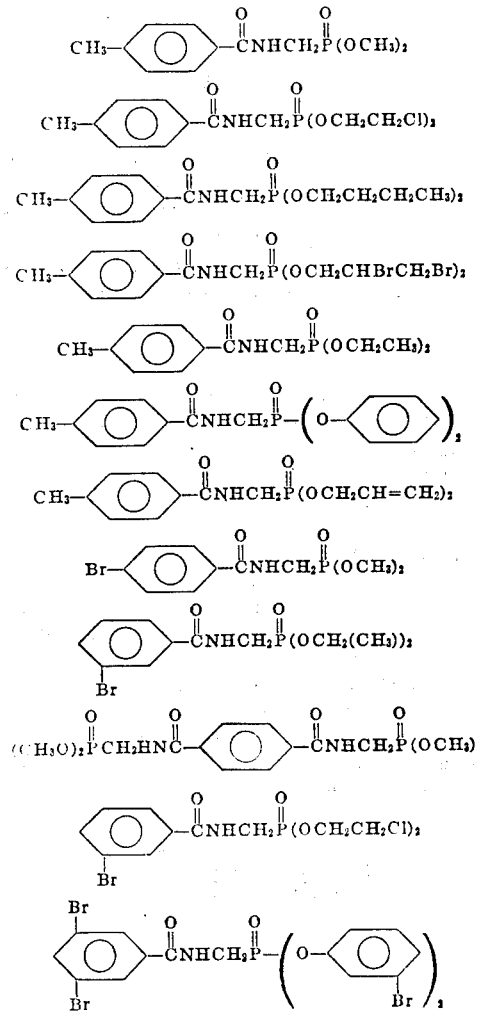

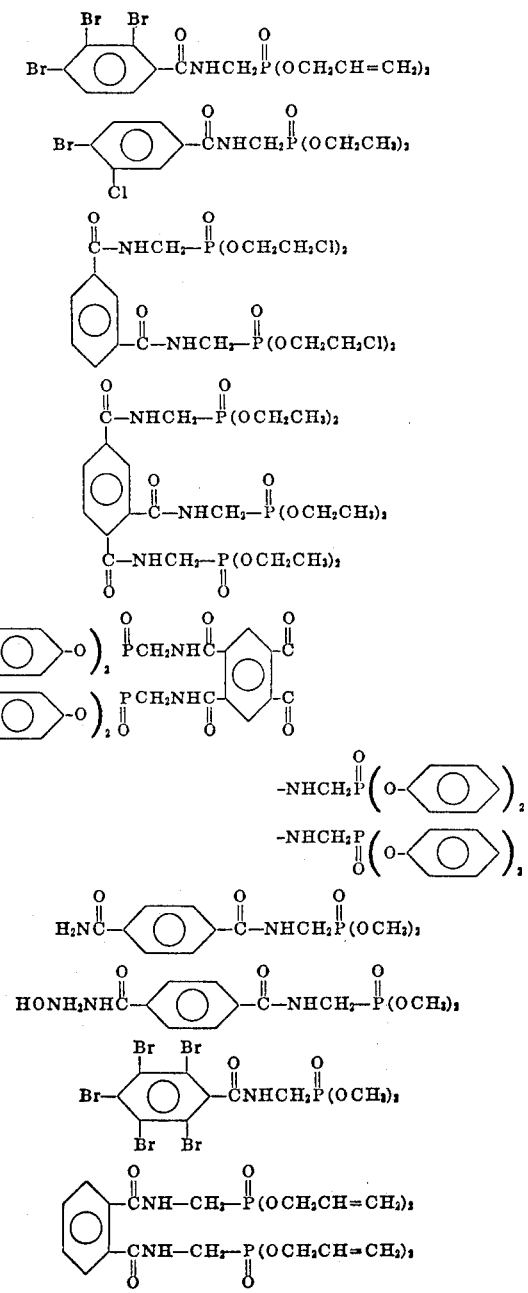

The synthesis of the compositions of the present invention is accomplished by reacting an N-hydroxymethyl aromatic amides of the formula

with a trialkyl phosphite of the formula (RO)₃P wherein R, m, n and X are as previously described in a suitable solvent. excess of the phosphite or neat. Typically, the reaction occurs at elevated temperatures and is continued for about 1 to about 12 hours. Temperatures are generally about 50°C. to about 160°C. Preferably reaction is continued from about 3 to about 6 hours at a temperature of about 80°C. to about 120°C. The solvent or other volatiles is thereafter stripped, or otherwise removed from the product. Suitable solvents include benzene, toluene, xylene, glymes, dimethylformamide, aliphatic or aromatic hydrocarbons. Typical N-hydroxymethyl aromatic amides operable as reactants herein include

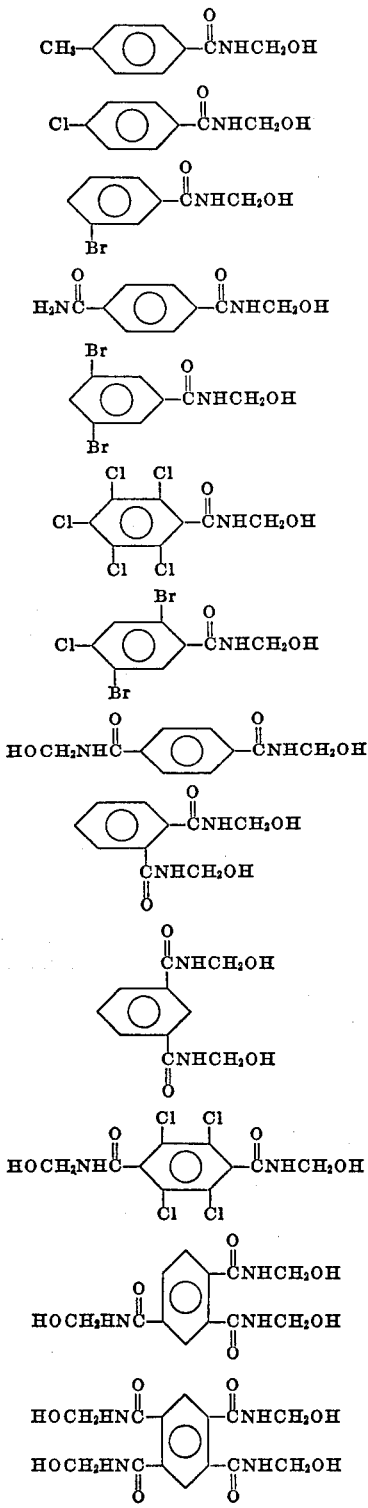

One or more of the novel compounds of this invention may be applied to textile materials by conventional finishing techniques such as by thermal induced pad curing so as to incorporate into the textile a flame retardant amount thereof. The compounds of this invention have advantages over the flame retardant agents of the prior art in that they may be used on a variety of textile materials of different chemical composition, and they may be applied by a variety of methods. They may be applied to materials in either the fiber or fabric form to give flame retarding materials with minimum detectable physical changes in the quality or hand of the textile material.

Cellulosic textile materials may be made flame retardant by way of a variety of methods. Products of this invention may be applied to cellulosic materials in several ways to give a durable flame retardant treatment. For example, the products of this invention may be reacted with formaldehyde to give N-hydroxymethyl derivatives which can react with cellulosic materials in a known manner. Alternatively aqueous mixtures of the products with formaldehyde, urea, trimethylol melamine or other known cellulose crosslinking agents may be applied to a cellulose substrate with the aid of an acidic catalyst by a pad dry process.

More preferably the N-hydroxymethyl derivative of the products of this invention prepared by the condensation of the products with formaldehyde, are mixed in an aqueous medium with trimethylol melamine and a Lewis acid catalyst such as $NH_4Cl$ or $Zn(NO_3)_2 \cdot 6H_2O$. The cellulosic material is immersed in an aqueous solution of the methylol derivative, trimethylol melamine, and $Zn(NO_3)_2 \cdot 6H_2O$ and squeezed on a two roll padder to 70–90% wet weight pick-up. The material is dried at 220°–270° F. for 1–3 minutes and cured at 300°–370° F. for 1–6 minutes in a circulating air oven. The sampler are then washed in hot water and dried. The finished samples have a flame retardant add on of about 5 to about 40% and preferably about 10 to about 25% by weight.

The flame retardant agents of this invention may be applied to various textiles such as cellulosic materials, proteinaceous materials and blends of cellulosic or proteinaceous materials and analogous man-made fibers. By cellulosic materials, applicant intends to embrace cotton, rayon, paper, regenerated cellulose and cellulose derivatives which retain a cellulose backbone of at least one hydroxy substituent per repeating glucose unit. By proteinaceous material applicant intends to embrace those textile materials comprising the functional groups of proteins such as the various animal wools, hairs and furs.

The flame retardant compounds or additives of the invention may be incorporated into thermoplastic, thermosetting or elastomeric resin compositions by any known method. That is to say, the flame retardant additive may be added to the resin by milling the resin and the additive on, for example, a two-roll mill, or in a Banbury mixer etc., or it may be added by molding or extruding the additive and resin simultaneously, or by merely blending it with the resin in powder form and thereafter forming the desired article. Additionally, the flame-retardant may be added during the resin manufacture, i.e., during the polymerization procedure by which the resin is made, provided the catalysts etc. and other ingredients of the polymerization system are inert thereto. Generally, the compounds of this invention may be incorporated into the thermoplastic resin in flame-retarding amounts, i.e. generally amounts ranging from about 5% by weight, to about 50% by weight, preferably from about 20% by weight, to about 40% by weight, based on the weight of the polymer, have been found sufficient.

Resins embraced within the scope of this invention include the homopolymers and copolymers of unsaturated aliphatic, alicyclic, and aromatic hydrocarbons. Suitable monomers are ethylene, propylene, butene, pentene, hexene, heptene, octene, 2-methylpropene-1, 3-methylbutene-1,4-methylpentene-1,4-methyl-hexene-1,5-methylhexene-1, bicyclo-(2.2.1)-2-heptene, butadiene, pentadiene, hexadiene, isoprene, 2,3-dimethylbutadiene-1,3, 2-methylpentadiene-1,3, 4-vinylcyclohexene vinylcyclohexene, cyclopentadiene, styrene and methylstyrene, and the like.

Other polymers in addition to the above-described olefin polymers that are useful in the invention include polyindene, indenecoumarone resins; polymers of acrylate esters and polymers of methacrylate esters, acrylate and methacrylate resins such as ethyl acrylate, n-butyl methacrylate, isobutyl methacrylate, ethyl methacrylate and methyl methacrylate; alkyd resins and paint vehicles, such as bodied linseed oil; cellulose derivatives such as cellulose acetate, cellulose acetate butyrate, cellulose nitrate, ethyl cellulose, hydroxyethyl cellulose, methyl cellulose and sodium carboxymethyl cellulose; epoxy resins; furan resins (furfuryl alcohol or furfural-ketone); hydrocarbon resins from petroleum; isobutylene resins (polyisobutylene)); isocyanate resins (polyurethanes); melamine resins such as melamine-formaldlehyde and melamine-ureaformaldehyde; oleo-resins phenolic resins such as phenol-formaldlehyde, phenolic - elastomer, phenolic-epoxy, phenolic-polyamide, and phenolic-vinyl acetals; polyamide polymers, such as polyamides, polyamide-epoxy and particularly long chain synthetic polymeric amides containing recurring carbonamide groups as an integral part of the main polymer chain; polyester resins such as unsaturated polyesters of dibasic acids and dihydroxy compounds, and polyester elastomer and resorcinol resins such as resorcinol-formaldehyde, resorcinol - furfural, resorcinol-phenol-formaldehyde, resorcinol-polyamide and resorcinol-urea; rubbers such as natural rubber, synthetic polyisoprene, reclaimed rubber, chlorinated rubber, polybutadiene, cyclized rubber, butadiene-acrylonitrile rubber, butadiene-styrene rubber, and butyl rubber; neoprene rubber (polychloroprene); polysulfides (Thiokol); terpene resins; urea resins; vinyl resins such as polymers of vinyl acetal, vinyl acetate or vinyl alcohol-acetate copolymer, vinyl alcohol, vinyl chloride, vinyl butyral, vinyl chloride-acetate copolymer, vinyl pyrrolidone and vinylidene chloride copolymers; polyformaldehyde; polyphenylene oxide; polymers of diallyl phthalates and phthalates; polycarbonates of phosgene or thiophosgene and dihydroxy compounds such as bisphenols, phosgene, thermoplastic polymers of bisphenols and epichlorohydrin (trade named Phenoxy polymers); graft copolymers and polymers of unsaturated hydrocarbons and unsaturated monomer, such as graft copolymers of polybutadiene, styrene and acrylonitrile, commonly called ABS resins; ABS polyvinyl chloride polymers, recently introduced under the trade name of Cycovin; and acrylic polyvinyl chloride polymers, known by the trade name Kydex 100.

The polymers of the invention can be in various physical forms, such as shaped articles, for example, moldings, sheets, rods, and the like; fibers, coatings, films and fabrics, and the like.

The compounds of this invention have been found to have particular utility in ABS resins and in elastomeric materials such as acrylic rubber; acrylonitrile-butadiene styrene terpolymers; butadiene-acrylonitrile copolymers; butyl rubber; chlorinated rubbers, e.g., polyvinyl chloride resins, chloroprene rubber, chlorosulfonated polyethylene; ethylene polymers, e.g., ethylene-propylene copolymers, ethylene-propylene terpolymers; fluorinated rubbers, butadiene rubbers, e.g., styrene-butadiene rubber, isobutylene polymers, polybutadiene polymers, polyisobutylene rubbers, polyisoprene rubbers; polysulfide rubbers; silicon rubbers; urethane rubbers; high styrene resins latices, high styrene resins, vinyl resins; sponge rubber; and the like.

It should be noted that it is also within the scope of the present invention to incorporate such ingredients as plasticizers, dyes, pigments, stabilizers, antioxidants, antistatic agents, and the like to the novel composition.

ASTM Test D2863-70, used in accordance with the following examples, generally provides for the comparison of relative flammability of self-supporting plastics by meauring the minimum concentration of oxygen in a slowly rising mixture of oxygen and nitrogen that will support combustion. The procedure encompasses supporting cylindrical test specimens 70–150 mm. × 8.0 mm. vertically in a glass tube fitted with controlled upward oxygen/nitrogen gas flow. The top of the specimen is ignited and oxygen flow is adjusted until it reaches that minimum rate at which the specimen is extinguished before burning 3 minutes or 50 mm. whichever happens first. The oxygen index ($n$) is then calculated as follows:

$$n, \text{percent} = (100 \times O_2)/(O_2 + N_2)$$

wherein $O_2$ is the volumetric flow of oxygen, at the minimal rate and $N_2$ is the corresponding volumetric flow rate of nitrogen.

A modification of ASTM Test D635-68 used in accordance with the following examples, generally provides for the comparison of burning rates, self-extinguishment and non-burning characteristics of plastics in the form of sheets, bars, plates or panels. The procedure encompasses preparing plastic samples of 150–200 mm. × 8 mm. with and without the subject flame retardant additive. Each sample is marked at points 1 inch and 4 inches from its end and held, marked end in the flame, at a 45° angle in a controlled burner flame (1 inch flame length) for two 30 second attempts. The movement of the flame up the length of the sample through the two points is measured for rate of burning, non-burning or self-extinguishing characteristics. A sample is rated SE (self-extinguishing) if the flame burns through the first point but extinguishes before reaching the second point. A sample is rated NB(non-burning) if, upon ignition it does not burn to the first point.

AATCC test method 34-1969, The Vertical Char Test, used in accordance with the following examples, generally provides for the comparison of relative flammability of 2¾ inch × 10 inch fabric test specimens when exposed to a controlled burner flame, under controlled conditions, for periods of 12.0 and 3.0 seconds. Charred specimens are thereafter subjected to controlled tearing tests, using tabulated weights, to determine the average tear length as representing the char length of the fabric. In addition, samples which are wholly consumed by the flame are rated (B) and samples which do not burn are rated (NB). For comparison purposes, it should be noted that untreated samples of the fabrics used in the examples of this case would be consumed for this test.

In all the examples of the application, the following general procedure was used except when otherwise specifically noted. Padding was done on a standard two roll laboratory padder at a gauge pressure of about 60 pounds per square inch in all cases. Drying and curing during processing were done with a standard laboratory textile circulating air oven. Washing and drying was done in a standard, home, top loading, automatic washer and dryer.

The following examples are set forth for purposes of illustration only and are not to be construed as limitations of the present invention except as set forth in the appended claims. All parts and percentages are by weight unless otherwise specified.

EXAMPLE I

Preparation of

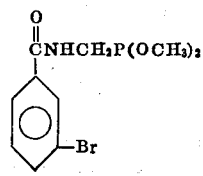

A 500 ml. flask was charged with 124 g. (1.0 mole) of trimethyl phosphite and was heated to about 100° C. 57.5 g. (0.25 mole) of 3-bromo-N-hydroxymethyl benzamide was then added to the reaction flask over a period of 5 minutes. The reaction mixture was then refluxed at about 95° for about 3 hours then stripped at 100° C. under a vacuum of 0.5 mm. mercury to give 81 g. of a colorless, viscous oil which by elemental analysis was confirmed to be the desired product.

EXAMPLE II

Preparation of

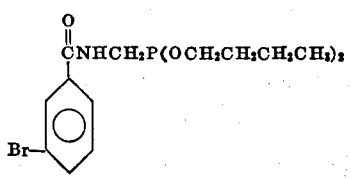

Following the procedure described in Example I 69 g. (0.3 mole) of 3-bromo-N-hydroxymethyl benzamide was refluxed with 80 g. (0.35 mole) of tri-n-butyl phosphite for about 5 hours at about 125° C. n-Butanol and excess tri-n-butyl phosphite were removed by stripping the reaction mixture at 115° C. under a vacuum of 0.5 mm. mercury. After stripping 121 g. of a pale yellow viscous liquid was obtained which was confirmed, by elemental analysis to be the desired product.

EXAMPLE III

Preparation of

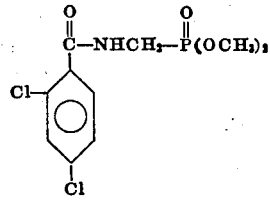

A 500 ml. flask, fitted with a reflux condenser, mechanical stirrer and thermometer, was charged with 124 g. (1.0 mole) of trimethyl phosphite and was heated to about 100° C. 61.8 g. (0.3 mole) of 2,4-dichloro-N-hydroxymethyl benzamide was added to the trimethyl phosphite, over a period of about 5 minutes. The homogeneous reaction mixture was then refluxed at about 93° C. for 3 hours and thereafter stripped, under a reduced pressure of about 0.5 mm. Hg at about 10° C., to give 93 g. of a tacky solid. Recrystallization of the solid from benzene of cyclohexane (1:1) gave 82.8 g. of dimethyl 2,4-dichlorobenzamidomethyl phosphonate.

EXAMPLE IV

Preparation of

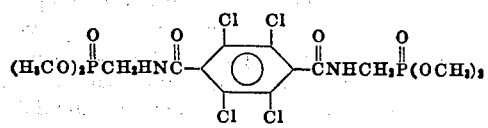

A 250 ml. flask was charged with 62 g. (0.5 mole) of trimethyl phosphite and was heated to about 100° C. 29 g. (0.1 mole) of bis-N,N-hydroxymethyl tetrachloroterephthalamide was addded to the flask and the reaction mixture was refluxed for about 6 hours and then cooled to room temperature. Unreacted solids were filtered off and the filtrate was stripped, at 70° C. under 2 mm. mercury of reduced pressure, to give 12.0 g. of a tacky solid product which was found, by infrared and nuclear magnetic resonance spectroscopy to be substantially pure desired product.

EXAMPLE V

Preparation of

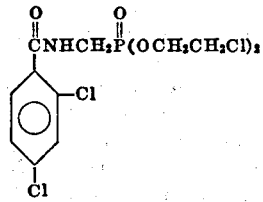

A 250 ml. flask was charged with 21.9 g. (0.1 mole) of 2,4-dichloro-N-hydroxymethyl benzamide and 27 g. (0.1 mole) of tris-2-chloroethyl phosphite. This reaction mixture was heated at about 130° C. for about 4 hours then stripped, at 100° C. under a vacuum of 1.3 mm. mercury, to give 41 grams of a white solid. The product was proven, by elemental and infrared and nuclear magnetic resonance spectroscopy, to be substantially pure desired product.

EXAMPLE VI

Preparation of

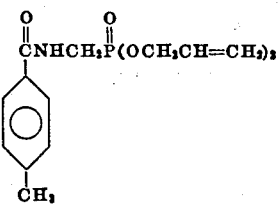

A 250 ml. flask was charged with 16.5 g. (0.1 mole) of N-hydroxymethyl-p-toluamide and 40.2 g. (0.2 mole) of triallyl phosphite and this reaction mixture was heated at about 130° C. for about 4 hours. Excess triallyl phosphite and allyl alcohol were removed by stripping, at 100° C. under a vacuum of 2 mm. mercury, to yield a thick yellow oil product. The product was confirmed by infrared and nuclear magnetic resonance spectroscopy and elemental analyses.

EXAMPLE VII

Preparation of

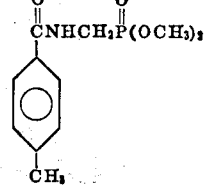

A 500 ml. flask, equipped with mechanical stirrer, thermometer and reflux condenser, was charged with 66 g. (0.4 mole) of N-hydroxymethyl p-toluamide and 124 g. (1.0 mole) of trimethyl phosphite. This reaction mixture was refluxed for about 4 hours then stripped, at 70° C. under 0.2 mm. mercury vacuum, to give 95 g. of a low melting solid. Elemental analysis with infrared and nuclear magnetic resonance spectroscopy confirmed the structure of the product.

EXAMPLE VIII

Preparation of

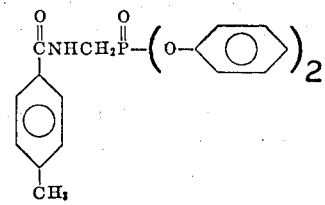

Triphenyl phosphite (62 g., 0.2 mole), was mixed with N-hydroxymethyl-p-toluamide in a 250 ml. round bottomed three necked flask fitted with mechanical stirrer, thermometer, and reflux condenser. The mixture was warmed to and maintained at about 130° C. for about 5 hours. After cooling the mixture was stripped, at 120° C. and 2 mm. Hg, to remove phenol and other volatile material. The stripped product was identified by elemental analysis as N-(diphenylphosphonomethyl)-p-toluamide and was obtained in 85.3% yield.

EXAMPLE IX

Preparation of

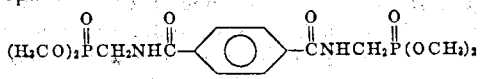

A mixture of 44.8 g. (0.2 mole) of N,N'-bis-hydroxymethyl terephthalamide and 124 g. (1.0 mole) of trimethyl phosphite was refluxed for about 6 hours. After the completion of the reaction the mixture was stripped, at 120° C. and 1 mm. Hg, to remove excess phosphite and other volatiles. The product was confrimed by infrared and nuclear magnetic resonance spectroscopy.

EXAMPLE X

Preparation of

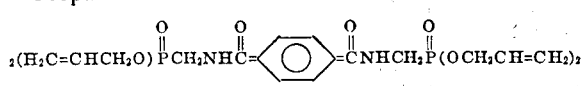

A mixture of 60.3 g. of triallyl phosphite and 22.4 g. of N,N-bis-hydroxymethyl terephthalamide was heated at about 130° C. for about 6 hours. The reaction mixture was striped, at 100° C. and 1 mm. Hg, to remove all volatile materials. A yellow liquid, which weighed 62.0 g., was isolated and confirmed as the desired product by spectroscopic and elemental analyses.

EXAMPLE XI

Forty parts of N-dimethylphosphonomethyl-2,4-dichlorobenzamide was mixed with 60 parts of polypropylene and dry blended for about 5 minutes. This mixture was then heated to a melt and mixed well in the molten state for about 15 minutes. The mixture was then allowed to cool to room temperature and the plastic composition was cut into small pieces. These pieces were placed slowly into a glass tube (9 mm.) immersed in a hot metal bath, the temperature of the bath being maintained above the melt temperature of the plastic composition. Pieces of the composition were added until the melt had a depth of approximately 200 mm. A metal rod was then placed in the tube with a weight attached and the tube cooled to solidify the composition. The composition was then removed from the tube and tested by ASTM tests D2863-70 and D635-68. The results of the testing are contained in Table I.

EXAMPLES XII–XXIX

Various additive compounds were mixed and treated with various resins according to the method of Example XI. Table I tabulates the results of testing by ASTM tests D2863-70 and D635-68 for Examples XII–XXIX.

EXAMPLE XXX

N-dimethyl phosphonomethyl-p-toluamide (25 g.) was mixed with 40% formalin solution (37.5 g.) and stirred overnight at pH 10. The pH was adjusted to 7.0 with hydrochloric acid and 3.1 g. of ammonium chloride and 14.0 g. of a 50% solution of a methylolated melamine added. 5.0 oz. sq. yd. cotton sheeting was immersed in the solution and the excess squeezed from the cloth by passing through a two roll laboratory padder at 60 lb. gauge pressure, to a wet pick-up of about 90%. The sheeting was then dried at about 250° F. for about 2 minutes and cured at about 340° F. for about 5 minutes in a circulating air oven. The sheeting was then washed by hand for about 5 minutes in a detergent (Tide) water mixture and tumble dried. A resin pick-up of 23.7% was calculated.

TABLE I

| Example | Polymer | Additive | Percent additive (by weight) | Flammability tests OI | Flammability tests D-635 |
|---------|---------|----------|------------------------------|-----------------------|--------------------------|
| XI | Polypropylene | Cl-C6H3(Cl)-CNHCH2P(OCH3)2 | 40 | 10.8 | SE |
| XII | Nylon | C6H5-CNHCH2P(OCH3)2 | 30 | 26.6 | NB |
| XIII | Polyethylene terephthalate | C6H5-CNHCH2P(OCH3)2 | 30 | 28 | NB |
| XIV | ABS | Br-C6H4-CNHCH2P(OCH3)2 | 30 | 24 | NB |
| XV | Nylon | Same as above | 30 | 25 | NB |
| XVI | Polyethylene terephthalate | do. | 30 | 38 | NB |
| XVII | ABS | Br-C6H4-CNHCH2P(OCH2CH2CH2CH3)2 | 40 | 22.3 | SE |

TABLE I-continued

| Example | Polymer | Additive | Percent additive (by weight) | Flammability tests OI | D-635 |
|---|---|---|---|---|---|
| XVIII | Nylon | Same as above | 40 | 20 | NB |
| XIX | Epoxy | do. | 30 | 29 | NB |
| XX | Polystyrene | $CH_3-\langle O \rangle-\overset{O}{\overset{\parallel}{C}}NHCH_2\overset{O}{\overset{\parallel}{P}}(OCH_3)_2$ | 30 | 23.3 | SE |
| XXI | Polyethylene terephthalate. | $CH_3-\langle O \rangle-\overset{O}{\overset{\parallel}{C}}NHCH_2\overset{O}{\overset{\parallel}{P}}(OCH_2CH=CH_2)_2$ | 40 | 29.4 | NB |
| XXII | Epoxy | $CH_3-\langle O \rangle-\overset{O}{\overset{\parallel}{C}}NHCH\overset{O}{\overset{\parallel}{P}}-(O-\langle O \rangle)_2$ | 30 | 24.7 | SE |
| XXIII | do. | $(H_3CO_2)\overset{O}{\overset{\parallel}{P}}CH_2HN\overset{O}{\overset{\parallel}{C}}-\langle O \rangle-\overset{O}{\overset{\parallel}{C}}NHCH_2\overset{O}{\overset{\parallel}{P}}(OCH_3)_2$ | 30 | 28 | SE |
| XXIV | Polyethylene terephthalate. | Same as above | 30 | 27.5 | |
| XXV | ABS | do. | 40 | | SE |
| XXVI | Polystyrene | $_2H_2C=CHCH_2O)\overset{O}{\overset{\parallel}{P}}CH_2HN\overset{O}{\overset{\parallel}{C}}-\langle O \rangle-\overset{O}{\overset{\parallel}{C}}NHCH_2\overset{O}{\overset{\parallel}{P}}(OCH_3CH=CH_2)_2$ | 40 | | SE |
| XXVII | ABS | Same as above | 30 | 24.3 | |
| XXVIII | Polystyrene | $Cl-\langle O \rangle_{Cl}-\overset{O}{\overset{\parallel}{C}}-NHCH_2\overset{O}{\overset{\parallel}{P}}(OCH_2CH_2Cl)_2$ | 40 | 23.8 | |
| XXIX | SBR | Same as above | 30 | 24.1 | SE |

The then treated sheeting was thereafter subjected to ASTM test D2863-70 and AATCC test 34-1969 with initial results as indicated in Table II. The cotton sheeting was thereafter subjected to four additional hand washes, as above described, and tested under AATCC test 34-1969.

EXAMPLES XXXI–XXXIII

Using the method of Example 30, 5 oz. per sq. yard cotton sheeting was treated with various compounds and subjected to ASTM test D2863-70 and AATCC test 34-1969. The results therefore are indicated in Table II.

EXAMPLE XXXIV

Rayon staple fiber was immersed in the solution described in Example XXX and squeezed on a two roll laboratory padder at about 60 lb. gauge pressure to a wet pick-up of about 100%. The fiber was then dried for about 3 minutes at about 250° F. and cured for about 10 minutes at about 350° F. in a circulating air oven. The fiber was then washed by hand for about 5 minutes in a hot detergent (Tide) water mixture and dried in the circulating air oven resulting in an add-on of about 13.8%. The fiber was then tested for flammability by holding one end of a treated sample in a benson flame for about 2 sec. and then removing and observing the sample. Treated samples self-extinguish immediately untreated samples are completely consumed.

The fiber was then further tested for durability by subjecting it to a 5 complete wash cycles in a standard, home type automatic washer using Tide detergent. Thereafter the fiber was tested for flammability as previously described. The results of testing is tabulated in Table II.

EXAMPLES XXXV–XXXIV

Using the method of Example XXXIV, rayon staple fiber was treated with various compounds and subjected to ASTM test D2863-70 and AATCC test 34-1969. The results are shown in Table II.

EXAMPLE XXXVII

N-diallyl phosphonomethyl-p-toluamide (19 g.) was mixed with 40% formalin solution (28.5 g.) and stirred overnight at pH 10. The pH was brought to 7.0 with hydrochloric acid and ammonium chloride ((2.4 g.) and a 50% solution of a methylolated melamine (10.9 g.) added.

6.0 oz. sq. yd. wool was immersed in the above solution, squeezed on a 2 roll laboratory padder to a wet pick-up of about 100% dried for about 2 minutes at about 250° F. and cured for about 5 minutes at about 350° F. in a circulating air oven. The wool was then washed for one wash cycle using Tide, in a standard, home type, automatic washer and tumble dried. The resin add-on was calculated as 25.3%.

The thus treated wool was thereafter subjected to ASTM test D2863-70 and AATCC test 34-1969. The wool was then subjected to four additional one cycle washings in a standard home type automatic washer, as above described, and thereafter tested by AATCC test 34-1969. Test results are tabulated in Table II.

TABLE II

| Example | Textile | Compound | Percent add-on | OI Initial | Flammability testing Initial | 5 home washes |
|---|---|---|---|---|---|---|
| XXX | Cotton (5 oz.) | $CH_3-\langle O \rangle-\overset{O}{\overset{\parallel}{C}}NHCH_2\overset{O}{\overset{\parallel}{P}}(OCH_3)_2$ | 23.7 | 22.2 | 4.9 | 6.0 |
| XXXI | Cotton (5 oz.) | $\langle O \rangle_{Br}-\overset{O}{\overset{\parallel}{C}}NHCH_2\overset{O}{\overset{\parallel}{P}}(OCH_3)_2$ | 54 | 27 | 1.0 | 3.1 |
| XXXII | Cotton (5 oz.) | $(H_3CO_2)\overset{O}{\overset{\parallel}{P}}CH_2HN\overset{O}{\overset{\parallel}{C}}-\langle O \rangle-\overset{O}{\overset{\parallel}{C}}NHCH_2\overset{O}{\overset{\parallel}{P}}(OCH_3)_2$ | 20.2 | 21.9 | 4.1 | 5.0 |
| XXXIII | Cotton (5 oz.) | Same as above | | 18.6 | H | H |
| XXXIV | Rayon (staple) | $CH_3-\langle O \rangle-\overset{O}{\overset{\parallel}{C}}NHCH_2\overset{O}{\overset{\parallel}{P}}(OCH_3)_2$ | 13.8 | 23 | SE | SE |
| XXXV | Rayon (staple) | $(CH_2=CH-CH_2O)_2\overset{O}{\overset{\parallel}{P}}CH_2HN\overset{O}{\overset{\parallel}{C}}-\langle O \rangle-\overset{O}{\overset{\parallel}{C}}NHCH_2\overset{O}{\overset{\parallel}{P}}(OCH_2CH=CH_2)_2$ | 10.8 | 22.7 | SE | SE |

TABLE II-continued

| Example | Textile | Compound | Percent add-on | Flammability testing OI Initial | Initial | 5 home washes |
|---|---|---|---|---|---|---|
| XXXVI | Rayon (staple) | Same as above | | 18.0 | B | B |
| XXXVII | Wool (6 oz.) | 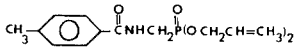 | 25.3 | 28 | 5.0 | 5.0 |

We claim:
1. A process for rendering resin compositions flame retardant which comprises applying to said resin a flame retardant amount of a compound of the formula:

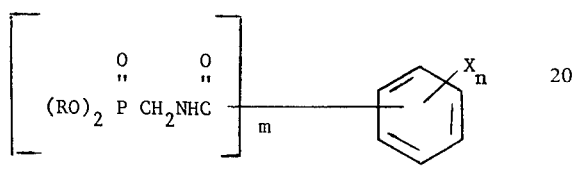

wherein R is selected from the group consisting of phenyl, lower alkenyl and halogen substituted and unsubstituted lower alkyl of 1-6 carbon atoms, X is selected from the group consisting of chlorine, bromine and lower alkyl of 1-6 carbon atoms, $m$ is an integer from 1-4 and $n$ is an integer from 0-5, provided that the sum of $m$ and $n$ is not greater than 6 and when $m$ is 1, $n$ is greater than 0.

2. The process of claim 1 wherein said resin is a thermoplastic composition.

3. The process of claim 1 wherein said resin is a thermosetting resin composition.

4. The process of claim 1 wherein said resin is an elastomeric composition.

5. An article comprising a resin compound and a fire retardant amount of a compound of the formula:

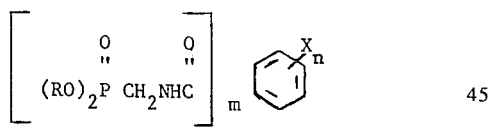

wherein R is selected from the group consisting of phenyl, lower alkenyl and halogen substituted and unsubstituted lower alkyl of 1-6 carbon atoms, X is selected from the group consisting of chlorine, bromine and lower alkyl of 1-6 carbon atoms, $m$ is an integer from 1-4 and $n$ is an integer from 0-5, provided that the sum of $m$ and $n$ is not greater than 6 and when $m$ is 1, $n$ is greater than 0.

6. The article of claim 5 wherein said compound is:

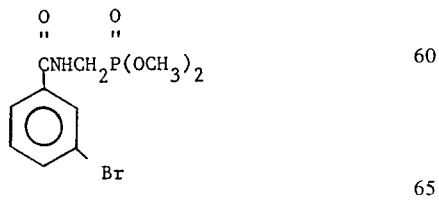

7. The article of claim 5 wherein said compound is:

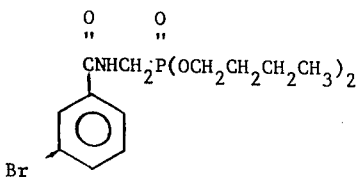

8. The article of claim 5 wherein said compound is:

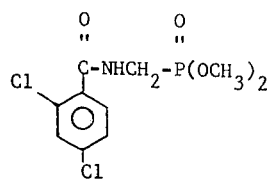

9. The article of claim 5 wherein said compound is:

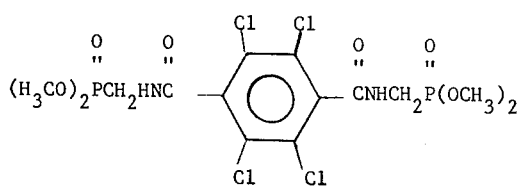

10. The article of claim 5 wherein said compound is:

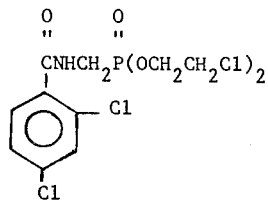

11. The article of claim 5 wherein said compound is:

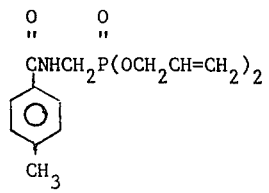

12. The article of claim 5 wherein said compound is:

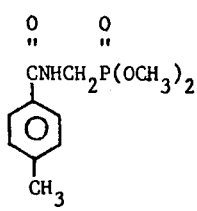
13. The article of claim 5 wherein said compound is:
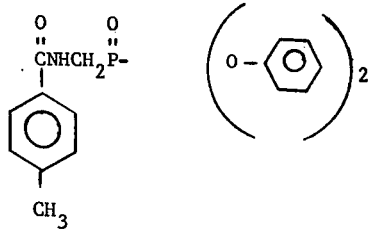
14. The article of claim 5 wherein said compound is:
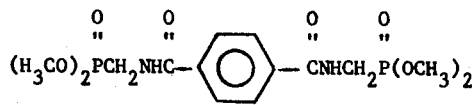
15. The article of claim 5 wherein said compound is:
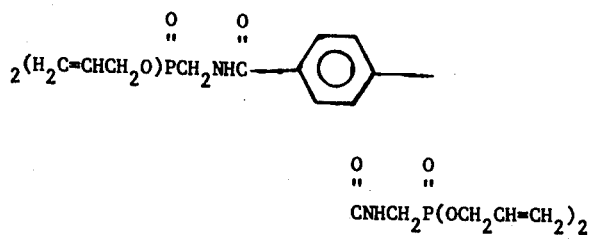
* * * * *

UNITED STATES PATENT OFFICE
CERTIFICATE OF CORRECTION

PATENT NO. : 3,935,162
DATED : January 27, 1976
INVENTOR(S) : Peter Golborn and James J. Duffy It is certified that error appears in the above-identified patent and that said Letters Patent are hereby corrected as shown below:

Column 1, line 26, ",X is greater than 0" should read ---,n is greater than 0---; line 42, "posprocesses" should read ---processes---. Column 2, line 57, "heating" should read ---treating---. Column 3, line 28, "lower alkyl, alkyl" should read ---lower alkyl, alkenyl---. Column 8, line 13, "meauring" should read ---measuring---. Table I, Example XXVI, "$_2H_2C$" should read ---$_2(H_2C$---. Table II, Example XXXIII, "18.6 $H^2H$" should read ---18.6 $^2B$ B---; Example XXXV, "10.8" should read ---19.8---.

Signed and Sealed this fourth Day of May 1976

[SEAL]

Attest:

RUTH C. MASON
Attesting Officer

C. MARSHALL DANN
Commissioner of Patents and Trademarks